United States Patent [19]

Rayboy

[11] Patent Number: 4,621,624

[45] Date of Patent: Nov. 11, 1986

[54] LINER FOR ORTHOPEDIC CAST

[76] Inventor: Eric R. Rayboy, 7361 N.W. 36 St., Lauderhill, Fla. 33319

[21] Appl. No.: 570,598

[22] Filed: Jan. 13, 1984

[51] Int. Cl.⁴ ............................................. A61F 7/00
[52] U.S. Cl. .................................... 128/83; 128/403; 128/82.1
[58] Field of Search ............... 128/DIG. 20, 400, 402, 128/403, 90, 91 R, 82.1

[56] References Cited

U.S. PATENT DOCUMENTS

| 3,683,902 | 8/1972 | Artemenko et al. | 128/82.1 |
| 4,013,069 | 3/1977 | Hasty | 128/20 X |
| 4,026,299 | 5/1977 | Sauder | 128/400 |
| 4,118,946 | 10/1978 | Tubin | 128/400 |
| 4,149,541 | 4/1979 | Gammons et al. | 128/400 |
| 4,308,862 | 1/1982 | Kalmar | 128/191 R |
| 4,326,533 | 4/1982 | Henderson | 128/402 |
| 4,338,944 | 7/1982 | Arkans | 128/400 |
| 4,375,217 | 1/1983 | Arkans | 128/DIG. 20 |

FOREIGN PATENT DOCUMENTS 02507829  9/1976  Fed. Rep. of Germany ........ 128/90

OTHER PUBLICATIONS

"Water-Cooled Body Casts Described"; Braces Today Newsletter of the Pope Foundation, Feb. 1956, Dr. Sullivan.

Primary Examiner—Dalton L. Truluck
Assistant Examiner—Karen Kaechele
Attorney, Agent, or Firm—Sanford J. Asman

[57] ABSTRACT

The Novel Liner for Orthopedic Cast is a device consisting of an inflatable bladder containing a matrix of flow channels with an inlet tube and an outlet tube for fluid flow. It serves four purposes:

(1) It is a cushion for the injured limb within the protective cast.
(2) It can administer a peristaltic massage to the affected area inside the cast to stimulate blood circulation.
(3) The temperature of the flow water can be adjusted to cool or warm the injury for alleviation of pain or discomfort.
(4) The liner can be partially inflated with air to compensate for atrophy of the immobilized limb, assuring a more correct fitting of the cast giving an extended period of usefulness.

This invention increases the efficacy and usefullness of the orthopedic cast.

6 Claims, 3 Drawing Figures

LINER FOR ORTHOPEDIC CAST

The present invention relates to an improvement in the standard liner used when forming an orthopedic cast around a broken bone.

Heretofore, there have been several materials used for cast liners, the most common of which is rolled cotton. These liners usually performed a single function, that of cushioning the injured limb during healing within the protective restriction of the cast. The present invention differs from those heretofore known in that it contains a ribbed bladder which can be filled with fluid. When incorporated in a cast, this novel liner can perform three additional functions:

(1) It can administer peristaltic massage to the encased body part, thus aiding blood circulation.
(2) Cool or warm water can be pumped through the liner to alleviate pain in the injured area.
(3) As the appendage atrophies and the cast becomes loose and ill-fitting, the liner can be expanded by partially filling it with air to fill this gap, thus permitting adjustable fit and increased useful lifetime for the cast.

Accordingly, the functionality of the cast liner will be greatly increased as will patient comfort.

IN THE DRAWINGS

Figure 2:
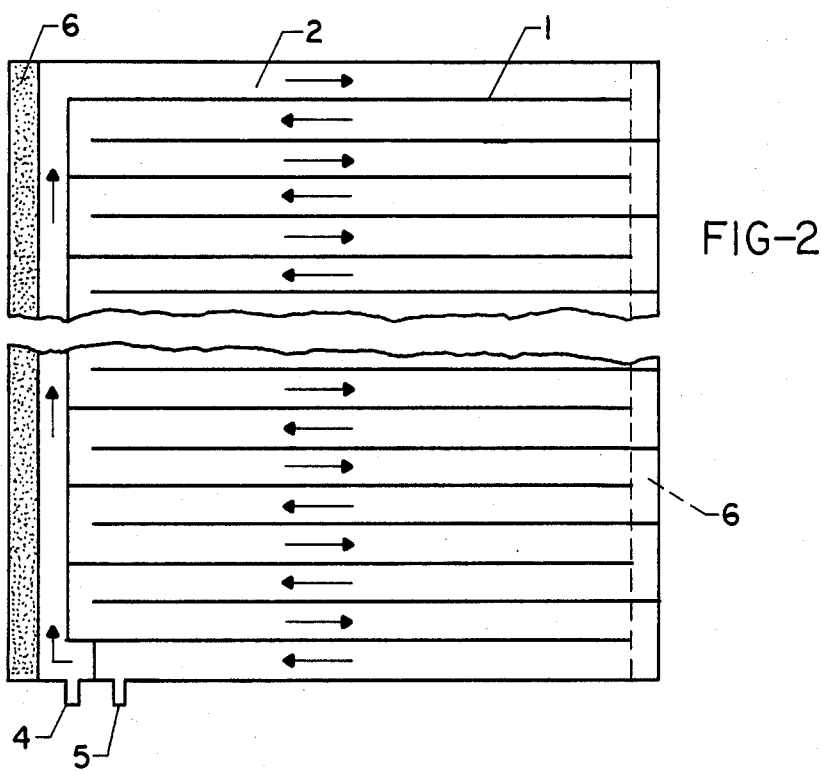
FIG. 2 is a top view of the invention spread out.
Figure 3:
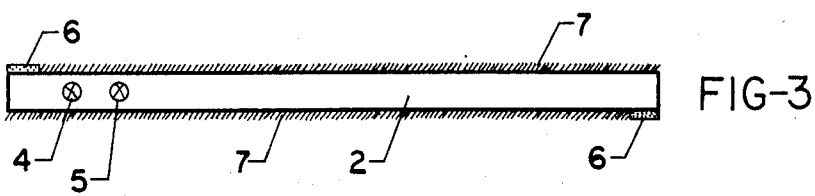
FIG. 3 is an end view.

Referring now to FIGS. 2 and 3, the cast liner is a bladder manufactured from two sheets of suitable, non-toxic plastic material. Each sheet has a fuzzy, wool-like finish 7 on the outer surface and a smooth finish on the inner surface; they are welded together along seams 1 using standard techniques to form a directed flow channel 2 extending from inlet tube 4 to outlet tube 5. Two strips of hook-type (male) fastening material, such as Velcro 6 are welded lengthwise along the top of one edge and the bottom of the opposite edge.

In actual usage, the cast liner is spread out and the injured limb is laid upon it lengthwise with the inlet tube 4 and outlet tube 5 located on the end of the cast closer to the patient's heart. The liner is then wrapped around the limb cylindrically by affixing the two Velcro strips 6 to the fuzzy surface 7. This gives a contoured, custom fit which does not restrict blood circulation.

Figure 1:
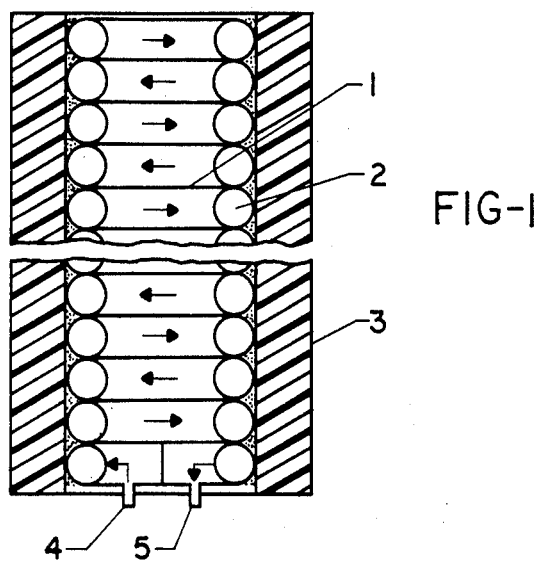
FIG. 1 is a cutaway view of the Novel Liner for Orthopedic Cast mounted inside a cast.

Referring now to FIG. 1, the cast material 3 is then wrapped around the liner and allowed to set. The fuzz 7 which contacts the patient's skin permits air circulation for greater comfort; the fuzz 7 which contacts the cast material 3 is ideal for maximizing bond strength between the cast and liner.

After the cast is set, the liner can be connected to a pumping device which forces water to flow through the bladder via inlet tube 4 and outlet tube 5; this flow is in the form of pulsations. These pulsations will cause the matrix of flow channels 2 to contract and expand in a peristaltic fashion, creating a mild masage action inside the cast. This in turn would enhance blood circulation in the stimulated areas. By varying the temperature of the flow water, soothing warmth or pain-alleviating cooling can be directed to the injury.

After such a treatment, the liner is drained and partially filled with air. This slight expansion in the thickness of the liner can be tailored to compensate for the gradual atrophy of the limb. This feature enables the doctor to maintain the good fit originally imparted to the cast for an extended period. Furthermore, the liner is inexpensive to mass produce and is disposable along with the cast.

Use of the present invention will expand the functionality, comfort, and useful lifetime of the orthopedic cast.

What is claimed is:

1. An orthopedic cast including an outer rigid cast material, an orthopedic cast liner of plastic material and a wool-like fuzzy surface located on the outside surface of said cast liner, said cast liner comprising a cylindrically-wrapped, rectangular bladder which includes an integral matrix of flow channels, said flow channels being adapted to contain a liquid and having an inlet tube and an outlet tube, whereby a liquid can be flowed into and through said bladder, wherein the outer surface of said bladder contains a wool-like, fuzzy surface texture, said orthopedic cast being formed around said wool-like outer surface on said bladder of said cast liner when said cast liner is in place on a patient's extremity, wherein the bond between said cast material and said wool-like surface of said cast liner is maximized.

2. The orthopedic cast liner of claim 1 wherein said wool-like fuzzy surface texture is comprised of the loop portion of a hook and loop fastening material.

3. The orthopedic cast liner of claim 1 wherein the outer surface of said bladder contains strips of hook and loop fasteners for affixing to itself when wrapped around an injured limb.

4. The orthopedic cast liner of claim 1 further comprising means for pumping said liquid into said bladder in pulsations whereby a peristaltic action may be created within said bladder.

5. The orthopedic cast liner of claim 1 wherein said liquid is water of elevated or lowered temperature to raise or lower the temperature of said bladder.

6. The orthopedic cast liner of claim 1 wherein said matrix of flow channels is inflated when said liquid is flowed into and through said bladder.

* * * * *